United States Patent [19]

Faggian et al.

[11] 4,322,561

[45] Mar. 30, 1982

[54] METHOD FOR THE PREPARATION OF CARBONYL COMPOUNDS

[75] Inventors: Lucio Faggian; Edoardo Platone, both of San Donato Milanese, Italy

[73] Assignee: Anio S.p.A., Palermo, Italy

[21] Appl. No.: 139,765

[22] Filed: Apr. 14, 1980

Related U.S. Application Data

[63] Continuation of Ser. No. 937,869, Aug. 29, 1978, abandoned.

[30] Foreign Application Priority Data

Sep. 14, 1977 [IT] Italy ............................... 27509 A/77

[51] Int. Cl.$^3$ ...................... C07C 45/64; C07C 45/61
[52] U.S. Cl. .................................... 568/391; 568/395; 568/458; 568/465; 260/465.1; 560/231; 560/51; 562/459
[58] Field of Search ............... 568/390, 395, 458, 465, 568/391; 260/465.1; 560/231, 51; 562/459

[56] References Cited

U.S. PATENT DOCUMENTS

| | | | |
|---|---|---|---|
| 2,440,800 | 5/1948 | Hanford et al. | 568/395 |
| 3,429,901 | 2/1969 | Blood et al. | 568/395 |
| 3,865,881 | 2/1975 | McMullen | 568/395 |
| 4,035,395 | 7/1977 | Stetter et al. | 568/390 |

FOREIGN PATENT DOCUMENTS

| | | | |
|---|---|---|---|
| 2142056 | 7/1972 | Fed. Rep. of Germany | 568/391 |
| 459455 | 5/1976 | U.S.S.R. | |

*Primary Examiner*—Natalie Trousof
*Assistant Examiner*—James H. Reamer
*Attorney, Agent, or Firm*—Morgan, Finnegan, Pine, Foley & Lee

[57] ABSTRACT

For preparing carbonyl compounds containing certain functional groups, a carbonyl compound is reacted with an unsaturated compound in the presence of a trivalent-manganese initiator and an amine. There is a positive coaction between the trivalent-Mn catalyst and the amine. Typically, 2-methyl-3-butene-2-ol is reacted with acetone in the presence of triethylamine and manganese triacetate (bihydrated) to obtain 2-methyl-heptane-2-ol-3-one. Yields and selectivities are more than satisfactory.

7 Claims, No Drawings

METHOD FOR THE PREPARATION OF CARBONYL COMPOUNDS

This is a continuation of application Ser. No. 937,869, filed Aug. 29, 1978, now abandoned.

This invention relates to a novel method for synthesizing compounds which may contain in their structure, in addition to the carbonyl group, one or more functional groups.

More particularly, the invention relates to a synthesis method which comprises the step of causing the addition of a carbonyl compound to an unsaturated compound which contains at least one unsaturation bond (double-bond or triple-bond) and possibly one or more functional groups, in the presence of a catalytic system composed of a manganese compound and an amine.

The radical addition reaction of bisulfite to various olefins, more particularly alpha-olefins, promoted by salts and oxides of transition metals and air has long been known. (M. S. Kharasch et al., J. Org. Chem., 3, 175 (1938) and JACS 61, 3092 (1939)).

With respect more particularly the radical addition (anti-Markownikow) of ketones to terminal olefins, the literature reports as follows:

The reaction between cyclohexanone and 1-octene initiated by UltraViolet radiations results in the corresponding addition compound with a yield which is as low as 18% (M. S. Kharasch et al., J. Org. Chem., 18, 1225 (1953)).

In the presence of organic peroxides or peroxyesters as the source of radicals, acetone leads to yields of 32% to 62% of the corresponding methyl-alkyl-ketones, together with telomers and products of splitting of the initiators (Z. Chem., 4, 177 (1964); J. Chem. Soc., 1918 (1965); Izv. Akad. Nauk, 2065, (1961)).

When operating in acetic acid as a solvent in the presence of acetates of transition metals (more particularly acetate of III-Mn, in an amount which is twice the stoichiometric quantity relative to the olefin) the corresponding methylalkyl ketones are obtained, in admixture with unsaturated ketones and gamma-ketoacetates as the principal products but with quite unsatisfactory conversions and selectivities. (JACS, 93, 524 (1971); Germ. Offenleg. 1936261 (1970); Izv. Akad. Nauk SSSR, Ser.Khim. 200 (1971)).

A similar reaction initiated by the acetate of III-Mn with no acetic acid present leads to products which cannot be distilled, in addition to the methyl-alkyl ketone, the latter being obtained in yields lower than the yields obtained with organic peroxides as the initiators (Zhur. Org. Khim., 8, 2467 (1972) and 11, 947 (1975)).

The addition of cyclopentanone to 1-octene in the presence of manganese as the catalyst and with air bubbled therethrough produces 2-octylcyclopentanone with a yield of 48%, whereas with cyclohexanone the yield is but one half this amount (Zhur. Org. Khim. 3, 2074–2075, (1967)). The addition of acetone to alpha olefins or to cyclohexene, or the addition of cyclopentanone and cyclohexanone to 1-octene and 1-decene, in the presence of AgO, Ag$_2$O or of oxides of transition metals (such as PbO$_2$, MnO$_2$, CuO, HgO and basic oxides of III-Ni, IV-Ni, III-Co and IV-Co) gives the corresponding methyl-alkyl ketones in yields comprising between 17% and 82% and selectivities of from 40% to 82%, referred to the olefin employed. (Tetr. Letters, 36, 3193 (1974); Czech. Chem. Comm., 41, 746 (1976); Synth. 315 (1976); Czech. Appl. 3917-74 (1974); Czech. Appl. 3807-75 (1975); Czech. Appl. 7762-75 (1975)).

It should be borne in mind that in the last case mentioned:
- the reaction is carried out in a nonaqueous medium and with no moisture being present;
- the reaction is always exclusively carried out on simple olefin which do not contain other reactive groups in their structure;
- the molar ratio of the catalyst to the olefin is comparatively high, being from 0.2 to 3 (preferably from 0.4 to 0.8) for AgO, and from 1 to 6 for other oxides of transition metals;
- variable but never negligible percentages of heavy telomers are always formed (e.g. 15% to 28% relative to the olefin).

From the foregoing, it can be seen that it has long been known and described in detail how to perform the radical addition of ketones to alpha-olefins and to cyclohexene.

In a copending patent application in the name of the present applicants an analogous reaction is described between a carbonyl compound and an unsaturated compound which also contains in its molecule one or more functional groups, and more particularly those group which are known as being reactive in radical positions (such as —OH). Characteristic advantages of this latter method are:
- absence of the heavy telomers referred to above;
- practicability of employing actual catalytic amounts of the reaction initiators;
- the obtaining of high values of selectivity with satisfactory yields.

It has now been found, and this is the subject matter of the present invention, that the reaction between a carbonyl compound and an unsaturated compound, the latter possibly containing in its molecule one or more reactive functional groups, more particularly groups which are reactive in a radical position (such as hydroxyls) can be carried out also in the presence of a catalytic system composed of a manganese compound and an amine.

The presence of a molecule such as that of an amine, which contains another reactive functional group, together with the presence of other reactive functional groups in the unsaturated molecule—more particularly in the alpha position relative to the unsaturation to which the carbonyl compound is added—could have suggested novel types of reactivity for the starting substrate, the result being a selectivity drop relative to the product of the 1:1 radical addition with possible formation of compounds wholly different from those contemplated heretofore for the reaction referred to above. With the types of compounds referred to above, and surprisingly enough, we have experienced an increase of the selectivity, the reaction conditions being the same, relative to similar reactions conducted without an amine being present.

In addition, the presence of the amine, in any event, makes the catalyst soluble in the reaction mixture and permits the reaction to take place in a homogeneous phase so as to obtain, as a result, all the advantages inherent therein.

These advantages can be summarized by stating that it is possible to carry out the reaction with no stirring and to feed both the reactants and the catalyst to the reactor continuously by means a pump.

Other advantages afforded by the present method are:

it practical to work under rigorously controlled pH conditions;

the catalyst can be dosed easily in solution, the same being true of the amine; and the exhausted catalyst can be separated merely by filtering it off from the reduced Mn compound formed during the reaction and which precipitates as it is being formed.

The present method can be accomplished by the use of:

a carbonyl compound which may be a ketone or an aldehyde of an aliphatic, alicyclic or aromatic nature and having a methyl or a methylene group in the alpha-position relative to the carbonyl, such as and more particularly an alpha-methyl ketone;

an unsaturated compound, which may contain one or more olefin bonds and/or one or more acetylenic bonds (preferably with an unsaturation in a terminal position) and may contain, moreover, one or more functional groups, among which, for example, are —OH, —OOCCH$_3$, —Cl, —OCH$_3$, —CN, —COOH, —COOR and the like.

Examples of such compounds are: 2-methyl-3-butene-2-ol; 2-methyl-3-butene-2-ol acetate; 2-methyl-2-methoxy-3-butene; 1-octene; 1-hexene, and others.

The catalyst is composed by III-manganese derivatives such as Mn(CH$_3$COO)$_3$.2H$_2$O; and an amine which can be selected from among the aliphatic primary, secondary, tertiary and cyclic amines, the aromatic amines or the thioamines. Examples of such compounds are tert.butylamine, diisopropylamine, triethylamine, piperidine, diphenylamine, thiourea.

The molar ratio of the carbonyl compound to the olefin varies from 550/1 to 3/1, and more particularly from 300/1 to 5/1.

The molar ratio of the catalyst to the olefin varies from 1/1 to 0.01/1.

The molar ratio of the amine to the olefin varies from 0.001 to 1.

The following examples, which illustrate the invention but do not limit it, explain the novel synthesis method for obtaining the compounds in question.

EXAMPLE 1

A one-liter stainless steel autoclave equipped with a magnetic stirrer is charged with 19.125 grams of 2-methyl-3-butene-2-ol (0.224 mol) which has been dehydrated on 5 A molecular sieves, 0.45 gram of triethylamine which has been distilled over KOH (0.0045 mol), 457 gram of acetone (7.8793 mol) which has been dehydrated on 5 A molecular sieves and then distilled, and 11.905 gram of Mn(CH$_3$COO)$_3$.2H$_2$O(0.044 mol).

The molar ratios ketone/olefin/catalyst/amine are 35.4/1/0.2/0.020. The reaction mixture is homogeneous and has a pH (measured with a glass-calomelan electrode connected to a pH-meter on an aqueous solution composed of 1 volume of reaction mixture and 3 volumes of distilled water) of 4.78.

Upon purging with nitrogen, the temperature of the autoclave is brought to 90° C. with stirring. After 3 hrs. 30 mins. reaction, the mixture is allowed to cool to room temperature. The pH of the solution is 4.02. A bottom residue is present, which is essentially Mn(CH$_3$COO)$_2$.

The conversion of 2-methyl-3-butene-2-ol is 31.9%: the selectivity in 2-methyl-heptane-2-ol-6-one is 84.9 molar percent referred to the 2-methyl-3-butene-2-ol which is used.

The analyses are effected with a Gas-Liquid Chromatograph Calibrated against a standard and by correcting the values of the area of the gas chromatographic peaks for the respective factors as obtained with a synthetic mixture.

EXAMPLES 2 TO 15

Using the same procedure as in Example 1, reactions are carried out and the results are tabulated in Table 1. The carbonyl compound used is acetone. The unsaturated compound used is 2-methyl-3-butene-2-ol and Mn(CH$_3$COO)$_3$.2H$_2$O is the manganese compound.

EXAMPLES 16 TO 18

Using the same procedure as in Example 1, three reactions are carried out and the results are tabulated in Table 2 Substrates other than the previous ones are used.

EXAMPLE 19

An autoclave of the type used for Example 1 is charged with 129 grams of acetone. After purging with nitrogen, the stirrer is started and heating is effected to raise the temperature to 100° C. During 2 hrs 30 mins the autoclave is fed by means of a piston metering pump with a solution formed of 258 grams of acetone, 12.7194 grams of 2-methyl-3-butene-2-ol, 7.9304 grams of catalyst Mn(CH$_3$COO)$_3$.2H$_2$O and 0.2095 grams of diisopropylamine. While feeding in the solution, the temperature is maintained at 100° C. and the reaction is discontinued after 30 minutes by discontinuing the feed mixture.

The feed ratios acetone/olefin/catalyst/amine on completion of the feed are 45/1/0.2/0.014.

The conversion of 2-methyl-3-butene-2-ol is 53.7% and the selectivity in 2-methyl-heptane-2-ol-6-one referred to 2-methyl-3-butene-2-ol is 86.4 molar percent.

The final pH of the solution is 4.24.

On completion of the the catalyst is separated in the form of Mn(CH$_3$COO)$_2$.

EXAMPLE 20

The same procedure as in the previous example is employed, except no stirring is applied.

The conversion is 54.2% and the selectivity 83.1 molar percent.

Examples 8 and 10, when carried out with no amine being used, illustrate conspicuously the selectivity improvement resulting from the use of an amine in a set of reactions which are conducted using the same types of reactants, reaction vessel and analytical methods.

It is apparent to anyone skilled in the art that reactions carried out in different time periods and with different reactants and apparatus may, even if the working conditions are the same, show limited discrepancies in the results. The difference between the reactions carried out with no amine and those carried out with amine are constant even within the usual variations of experimental values. The best mode for making this difference conspicuous, a mode which is continuous but reproducible, is the one adopted by the present applicants, that is, to effect an absolutely homogeneous series of synthesis.

TABLE 1

| Ex. N° | A/B/C/Amine | Amine | pH$_i$ | pH$_f$ | Time hrs | Temp. °C. | Conversion % | Selectivity mol % |
|---|---|---|---|---|---|---|---|---|
| 2 | 30/1/0.2/0.0054 | Net$_3$ | 4.52 | 3.57 | 4 | 90 | 47.5 | 71.5 |
| 3 | 30/1/0.2/0.0072 | (i-prop)$_2$NH | 4.63 | 4.08 | 3 | 90 | 58.0 | 70.6 |
| 4 | 30/1/0.2/0.013 | (i-prop)$_2$NH | 4.65 | 3.95 | 3 | 90 | 53.5 | 80.5 |
| 5 | 30/1/0.2/0.0073 | (i-prop)$_2$NH | 4.63 | 3.66 | 3 | 100 | 58.6 | 69.4 |
| 6 | 30/1/0.2/0.013 | (i-prop)$_2$NH | 4.66 | 3.92 | 3 | 100 | 54.6 | 74.5 |
| 7 | 30/1/0.2/0.0287 | (i-prop)$_2$NH | 4.68 | 4.31 | 2 | 100 | 39.1 | 85.3 |
| 8 | 30/1/0.2/— | (absent) | n.d. | 3.29 | 3 | 100 | 62.5 | 68.2 |
| 9 | 60/1/0.2/0.014 | (i-prop) NH | 4.59 | 3.92 | 3 | 100 | 63.7 | 90.5 |
| 10 | 60/1/0.2/— | (absent) | 4.15 | 3.73 | 3 | 100 | 74.2 | 78.8 |
| 11 | 30/1/0.2/0.014 | (t-but) NH$_2$ | 4.77 | 4.02 | 2 | 90 | 49.6 | 78.7 |
| 12 | 30/1/0.2/0.014 | (t-but) NH$_2$ | 4.61 | 3.95 | 3 | 90 | 59.2 | 79.0 |
| 13 | 30/1/0.2/0.007 | (t-but) NH$_2$ | 4.48 | 3.92 | 3 | 100 | 60.5 | 71.6 |
| 14 | 30/1/0.2/0.014 | (t-but) NH$_2$ | 4.71 | 3.95 | 3 | 100 | 58.4 | 71.0 |
| 15 | 30/1/0.2/0.0282 | (t-but) NH$_2$ | 4.56 | 4.28 | 3 | 100 | 54.2 | 70.2 |

The values of A/B/C/Amine are the molar ratios of the reacting species
A is acetone; B is 2-methyl-3-butene-2-ol; C is Mn (OAC)$_3$ . 2H$_2$O; pH$_i$ is the pH as measured at the start of the reaction; pH$_f$ is the pH as measured on completion of the reaction as indicated in Example 1.
The values of Col. 8 are the values of conversion (%) of 2-methyl-3-butene-2-ol.
The values of Col. 9 are the selectivities in molar percentage of 2-methyl-heptane-2-ol-6-one relative to 2-methyl-3-butene-2-ol.

TABLE 2

| Ex. N° | A/olefine/C/D | Olefine | pH$_i$ | pH$_f$ | Time hrs | Temp. °C. | Conversion % | Selectivity molar% |
|---|---|---|---|---|---|---|---|---|
| 16 | 30/1/0.2/0.01 | 1-octene | 4.07 | 4.12 | 3 | 100 | 48.6 | 50.8 |
| 17 | 60.8/1/0.2/0.014 | 2-methyl-2-methoxy-3-butene | 4.66 | 3.98 | 3 | 100 | 42.8 | 67.6 |
| 18 | 60.9/1/0.2/0.014 | 1-octene | 4.72 | 4.27 | 3 | 100 | 56.0 | 63.4 |

The values of A/oleifine/C/D are the molar ratios between the reacting species.
A and C have the same meanings as in Table 1.
D is diisopropylamine.
The values of Col. 8 are the percentage conversion of the olefine.
The values of Col. 9 are the molar selectivities of undecane-2-one for examples 16 and 18 and of 2-methyl-2-methoxyheptane-6-one for Example 17 referred to the respective olefines.

We claim:

1. A method for the preparation of carbonyl compounds which may also contain in their structure one or more other functional groups, including groups which are reactive in radical reactions, comprising the step of reacting a ketone selected from the group consisting of acetone and methylethyl ketone and an olefinically unsaturated compound having one or more hydrogen atoms thereof substituted by one or more functional groups selected from hydroxy and alkoxy with each other in the presence of catalytic amounts of Mn acetate in a molar ratio relative to said olefinically unsaturated compound of from 0.01:1 to 1:1 and an amine in a molar ratio relative to said olefinically unsaturated compound of from 0.001:1 to 1:1.

2. A method according to claim 1 wherein the olefinically unsaturated compound is selected from 2-methyl-3-butene-2ol, 2-methyl-2-methoxy-3-butene, 1-octene and 1-hexene.

3. A method according to claim 1 wherein the amine is selected from primary, secondary and tertiary aliphatic, alicyclic and aromatic amines.

4. A method according to claim 3 wherein the amine is diisopropylamine.

5. A method according to claim 1 wherein the ketone is acetone.

6. A method according to claim 1 wherein the ketone is methylethyl ketone.

7. A method according to claim 3 wherein the amine is tertiary butylamine.

* * * * *

UNITED STATES PATENT AND TRADEMARK OFFICE
CERTIFICATE OF CORRECTION

PATENT NO. : 4,322,561

DATED : March 30, 1982

INVENTOR(S) : Lucio Faggian et al.

It is certified that error appears in the above-identified patent and that said Letters Patent is hereby corrected as shown below:

On the title page, Assignee should read

-- (73) Assignee: ANIC S.p.A, Palermo, Italy --

Signed and Sealed this

Third Day of August 1982

[SEAL]

Attest:

Attesting Officer

GERALD J. MOSSINGHOFF

Commissioner of Patents and Trademarks